United States Patent [19]

Green

[11] Patent Number: 4,531,966
[45] Date of Patent: Jul. 30, 1985

[54] HERBICIDE COMPOSITIONS

[75] Inventor: Laddie L. Green, San Jose, Calif.

[73] Assignee: Stauffer Chemical Company, Westport, Conn.

[21] Appl. No.: 474,221

[22] Filed: Mar. 11, 1983

[51] Int. Cl.³ .................................... A01N 25/32
[52] U.S. Cl. ........................................ 71/93; 71/88; 71/90
[58] Field of Search ............................ 71/93, 88, 90

[56] References Cited

U.S. PATENT DOCUMENTS

| | | | |
|---|---|---|---|
| 3,959,304 | 5/1976 | Teach | 71/88 |
| 4,127,405 | 11/1978 | Levitt | 71/93 |
| 4,343,649 | 8/1982 | Sweetser | 71/93 |
| 4,441,914 | 4/1984 | Duerksen | 71/95 |

OTHER PUBLICATIONS

Short Communications, Parker et al., Tropical Pest Management, vol. 27, No. 1, (1981), pp. 139–140.

*Primary Examiner*—Catherine L. Mills
*Attorney, Agent, or Firm*—Paul R. Martin; Elliott L. Fineman

[57] ABSTRACT

Herbicide compositions comprising an herbicidally effective amount of a compound having the formula

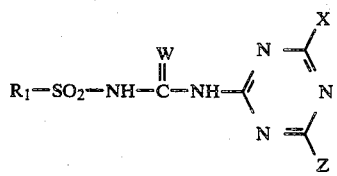

wherein $R_1$ is

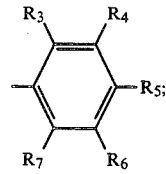

$R_3$ and $R_6$ are independently hydrogen, halogen, alkyl, alkoxy, nitro, trifluoroalkyl, cyano, $CH_3S(O)_n-$ or $CH_3CH_2S(O)_n-$; $R_4$ is hydrogen, halogen, or alkyl; $R_5$ is hydrogen, halogen, alkyl or alkoxy; $R_7$ is hydrogen, halogen, alkyl or alkoxy; W is sulfur or oxygen; n is 0, 1 or 2; X is hydrogen, halogen, alkyl, alkoxy, trifluoroalkyl, thioalkyl or alkoxyalkyl; and Z is alkyl or alkoxy; or their agriculturally acceptable salts; and an antidotally effective amount of an antidote compound having the formula

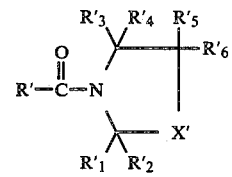

in which X' is oxygen or sulfur, R' is haloalkyl having 1 to 10 carbon atoms, inclusive, and the term halo includes chloro and bromo substitutions, alkyl having 1 to 10 carbon atoms, inclusive, or alkylthio having 1 to 4 carbon atoms, inclusive, $R'_1$, $R'_2$, $R'_3$, $R'_5$ and $R'_6$ are independently selected from the group consisting of hydrogen, lower alkyl having 1 to 4 carbon atoms, inclusive, alkoxyalkyl having a total of 2 to 4 carbon atoms, inclusive, and lower alkylol having 1 to 4 carbon atoms, inclusive, and their use in controlling weeds while improving crop protection.

15 Claims, No Drawings

HERBICIDE COMPOSITIONS

FIELD OF THE INVENTION

The invention pertains to novel compositions of benzenesulfonamides and oxazolidines and their use for selective herbicidal action.

BACKGROUND OF THE INVENTION

Among the many herbicide compounds the benzenesulfonamides have shown a particularly high degree of commercial success. In particular, certain of the benzenesulfonamides in amounts approaching as low as 0.0156–0.03125 pounds per acre (0.0174–0.0350 kilograms/hectare (kg/ha)) have proven to be effective herbicides in some crop applications. It has been found, however, that the effectiveness of these compounds is tempered by their poor selectivity with respect to certain commercially important crops; that is the benezenesulfonamides also injure crop plants in addition to the weeds they are intended to control.

DESCRIPTION OF THE INVENTION

It has been observed that plants can be protected against injury caused by the benezenesulfonamides having the general formula

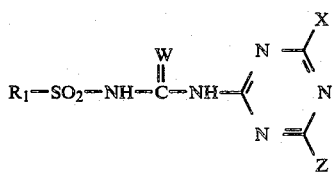

wherein
$R_1$ is

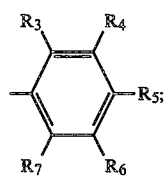

$R_3$ and $R_6$ are independently hydrogen, alkyl, alkoxy nitro, trifluoroalkyl, cyano, $CH_3S(O)_n$— or $CH_3CH_2S(O)_n$—;
$R_4$ is hydrogen, halogen, or alkyl;
$R_5$ is hydrogen, halogen, alkyl or alkoxy;
$R_7$ is hydrogen, halogen, alkyl or alkoxy;
W is oxygen or sulfur;
n is 0, 1 or 2;
X is hydrogen, halogen, alkyl, alkoxy, trifluoroalkyl, thioalkyl or alkoxyalkyl; and
Z is alkyl or alkoxy; or their agriculturally suitable salts; by adding to the habitat of the crop plant at antidotally effective amount of a compound having the general formula

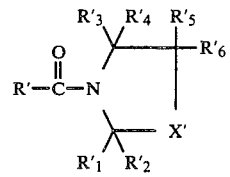

in which X' is oxygen or sulfur, R' is haloalkyl having 1 to 10 carbon atoms, inclusive, and the term halo includes chloro and bromo substitutions, alkyl having 1 to 10 carbon atoms, inclusive, or alkylthio having 1 to 4 carbon atoms, inclusive, $R'_1$, $R'_2$, $R'_3$, $R'_5$ and $R'_6$ are independently selected from the group consisting of hydrogen, lower alkyl having 1 to 4 carbon atoms, inclusive, alkoxyalkyl having a total of 2 to 4 carbon atoms, inclusive, and lower alkylol having 1 to 4 carbon atoms, inclusive.

More particularly, it has been observed that plants can be protected against injury caused by the benzenesulfonamides having the general formula

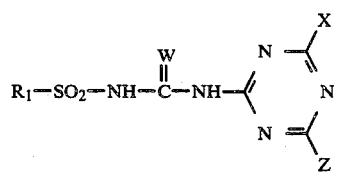

wherein
$R_1$ is

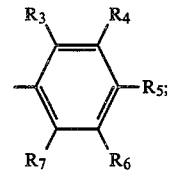

$R_3$ and $R_6$ are independently hydrogen, fluorine, chlorine, bromine, iodine, alkyl of 1–4 carbon atoms, alkoxy of 1,4 carbon atoms, nitro, trifluoromethyl, cyano, $CH_3S(O)_n$— or $CH_3CH_2S(O)_n$—;
$R_4$ is hydrogen, fluorine, chlorine, bromine, or methyl;
$R_5$ is hydrogen, fluorine, chlorine, bromine, methyl or methoxy;
$R_7$ is hydrogen, fluorine, chlorine, bromine, alkyl of 1–2 carbon atoms, or alkoxy of 1–2 carbon atoms;
W is oxygen or sulfur;
n is 0, 1 or 2;
X is hydrogen, chlorine, bromine, methyl, ethyl, alkoxy of 1–3 carbon atoms, trifluoromethyl, $CH_3S$— or $CH_3OCH_2$—; and
Z is methyl or methoxy; or an agriculturally suitable salt thereof; provided that:
(a) when $R_5$ is other than hydrogen at least one of the $R_3$, $R_4$, $R_6$ and $R_7$ is other than hydrogen, and at least two of $R_3$, $R_4$, $R_6$ and $R_7$ must be hydrogen;
(b) when $R_5$ is other than hydrogen and all of $R_3$, $R_4$, $R_6$ and $R_7$ are other than hydrogen, then all of $R_3$, $R_4$, $R_6$ and $R_7$ must be either chlorine or methyl; and (c) when R₃ and R₇ are both hydrogen, at least one of R₄, R₅, or R₆ must be hydrogen;
by adding to the habitat of the crop plant an antidotally effective amount of a compound having the general formula

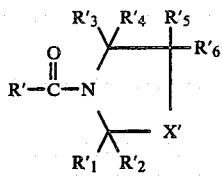

in which X' is oxygen or sulfur, R' is haloalkyl having 1 to 10 carbon atoms, inclusive, and the term halo includes chloro and bromo substitutions, alkyl having 1 to 10 carbon atoms, inclusive, or alkylthio having 1 to 4 carbon atoms, inclusive, R'₁, R'₂, R'₃, R'₅ and R'₆ are independently selected from the group consisting of hydrogen, lower alkyl having 1 to 4 carbon atoms, inclusive, alkoxyalkyl having a total of 2 to 4 carbon atoms, inclusive, and lower alkylol having 1 to 4 carbon atoms, inclusive.

The synthesis of the benzenesulfonamides of the above-mentioned general formula is well known to those skilled in the art and in particular is disclosed in U.S. Pat. No. 4,127,405. The synthesis of the oxazolidine compounds of the above-mentioned general formula is also well known to those skilled in the art and in particular is disclosed in U.S. Pat. No. 3,989,503. Both of these U.S. patents are herein incorporated by reference.

Among the benzenesulfonamide herbicide compounds, 2-chloro-N-[(4-methyloxy-6-methyl-1,3,5-triazin-2-yl)aminocarbonyl]-benzene sulfonamide, having the structural formula

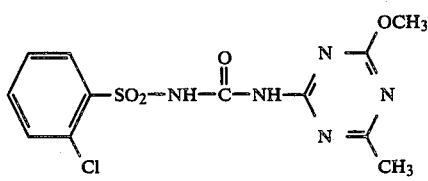

is known to be a particularly active herbicide. It has been found that when 2-chloro-N-[(4-methyloxy-6-methyl-1,3,5-triazin-2-yl)aminocarbamyl]-benzene sulfonamide is used in combination with antidote compounds having the general formula

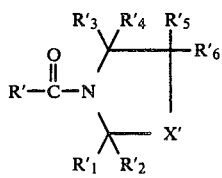

in which X' is oxygen or sulfur, R' is haloalkyl having 1 to 10 carbon atoms, inclusive, and the term halo includes chloro and bromo substitutions, alkyl having 1 to 10 carbon atoms, inclusive, or alkylthio having 1 to 4 carbon atoms, inclusive, R'₁, R'₂, R'₃, R'₅ and R'₆ are independently selected from the group consisting of hydrogen, lower alkyl having 1 to 4 carbon atoms, inclusive, alkoxyalkyl having a total of 2 to 4 carbon atoms, inclusive, and lower alkylol having 1 to 4 carbon atoms, inclusive and, in particular 2,2,5-trimethyl-3-dichloroacetyloxazolidine, injury to the crop plant is reducted.

DESCRIPTION OF THE PREFERRED EMBODIMENTS

The compositions of this invention were tested in the following manner.

EXAMPLE I

Seed Treatment

One hundred milligrams (100 mg) of 2,2,5-trimethyl-3-dichloroacetyloxazolidine was dissolved in one milliliter (1 ml) of acetone. This solution was added to 20 grams (g) of seeds of each of the crops listed herein below. Plastic flats were filled with Felton loamy sand soil. A one pint sample of soil from each flat was removed and retained to be used to cover the seeds after planting. The soil was then leveled and rows one-quarter inch deep were made in each flat. Flats were seeded with DeKalb XL-43A corn (*Zea maize*), anza wheat (*Triticum aestivum*), Bragg soybeans (*Glycine max*), sorghum R-10 (*Sorghum vulgare*), Acala cotton (*Gossypium hirsutum*), USH-9 sugarbeets (*Beta vulgare*), and CM-72 Barley (*Hordeum vulgare*). Seeds were then covered with the pint soil sample removed prior to seeding. The flats were then placed on greenhouse benches where the temperatures were maintained between 75°-90° F. The soil was watered by sprinkling to ensure good plant growth. Nineteen mg of the herbicide compound dissolved in 100 milliliters (ml) of acetone was mixed with 100 ml of water. This solution was sprayed on the plants three weeks after seeding at a rate of 0.0624 pounds per acre (0.0698 kilograms per hectare) for each flat. The condition of the plants was evaluated 3 weeks after treatment with the herbicide. The results of this evaluation are reported in Table I.

TABLE I

Herbicide: 2-chloro-N—[(4-methyloxy-6-methyl-1,3,5-triazin-2-yl)-aminocarbonyl]-benzene sulfonamide
Antidote: 2,2,5-trimethyl-3 dichloroacetyloxazolidine
Method: 0.5% Seed Treatment

| Crop | % Crop Injury | | % Improvement | |
|---|---|---|---|---|
| | U (%) | T (%) | U-T (%) | U-T/U (%) |
| corn | 65 | 45 | 20 | 30 |
| wheat | 37.5 | 100 | — | — |
| soybeans | 80 | 90 | — | — |
| sorghum | 60 | 90 | — | — |
| cotton | 55 | 60 | — | — |
| rice | 62.5 | 50 | 12.5 | 20 |
| sugar beets | 100 | 100 | — | — |
| barley | 35 | 50 | — | — |

U = Treated with herbicide but not treated with antidote.
T = Treated with herbicide and antidote.
— = Injury rates ≧ U.

EXAMPLE II

Post-emergence testing of the antidote compound and the herbicide control compound was carried out as follows.

Crop seeds were prepared and grown in flats under the conditions as in Example 1 hereinabove except that the seeds were untreated prior to planting. Nineteen days after planting the seed plants were treated with the herbicide compound and antidote compound prepared as follows. A stock solution of the herbicide compound containing 56 mg of the herbicide compound in 150 ml of acetone and 150 ml of water was prepared. Two stock solutions of the antidote were prepared: one containing 900 mg of the antidote compound in 150 ml of acetone and 150 ml of water, and a second containing 4500 mg of the antidote compound in 150 ml of acetone and 150 ml of water. Twenty ml of the herbicide stock solution was admixed with 20 ml of each of the antidote stock solutions and was sprayed on the crop plants at the rate of either one pound or 5 pounds per acre (1.12 or 5.60 kg/ha) for the antidote compound and 0.0625 pounds per acre (0.0698 kg/ha) for the herbicide compound, as indicated in Table II. The condition of the plants was evaluated three weeks after spraying. The results of the spraying are reported in Table II.

TABLE II

Herbicide: 2-chloro-N—[(4-methyloxy-6-methyl-1,3,5-triazin-2-yl)-aminocarbonyl]-benzene sulfonamide at 0.0625 pound per acre
Antidote: 2,2,5-trimethyl-3-dichloroacetyl oxazolidine

| Antidote Rate lb/A | Crop | % Injury U (%) | % Injury T (%) | % Improvement U-T (%) | % Improvement U-T/U (%) |
|---|---|---|---|---|---|
| 1 | corn | 65 | 10 | 55 | 84 |
|   | wheat | 32.5 | — | — | — |
|   | soybeans | 80 | 60 | 20 | 25 |
|   | sorghum | 60 | 35 | 25 | 41 |
|   | cotton | 55 | — | — | — |
|   | rice | 62.5 | 50 | 12.5 | 20 |
|   | sugarbeets | 100 | — | — | — |
|   | barley | 35 | — | — | — |
| 5 | corn | 65 | 15 | 50 | 76 |
|   | wheat | 32.5 | — | — | — |
|   | soybeans | 80 | 70 | 10 | 12.5 |
|   | sorghum | 60 | 40 | 20 | 33 |
|   | cotton | 55 | — | — | — |
|   | rice | 62.5 | 50 | 12.5 | 20 |
|   | sugarbeets | 100 | — | — | — |
|   | barley | 35 | 30 | 5 | 15 |

U = Treated with herbicide but not treated with antidote.
T = Treated with herbicide and antidote.
— = dashes indicated injury rates ≧U.

EXAMPLE III

Herbicidal Compositions Used on Corn

Flats were prepared as in Example II above except that they were seeded with three strains of DeKalb corn: XL43A, XL55 and XL379. The seeded flats were grown for three weeks under the same conditions as Examples I and II above. Stock solutions of the herbicides were prepared as follows.

One hundred-thirteen mg of the herbicide compound was dissolved in 300 ml of acetone to which was added 300 ml of water. When admixed with the antidote stock solutions (described below) this stock solution was applied at a rate of 0.079 pounds per acre (0.0868 kg/ha).

Two-hundred twenty-five mg of the herbicide compound were mixed with 300 ml of acetone to which was added 300 ml of water. When admixed with the antidote stock solutions (described below) this stock solution was applied at a rate of 0.158 pounds per acre (0.176 kg/ha).

Antidote stock solutions were prepared as follows: Stock Solution A was prepared by dissolving 300 mg of the antidote compound in 25 ml of acetone and adding 25 ml of water. Stock Solution B was prepared by dissolving 150 mg of the antidote compound in 25 ml of acetone and adding 25 ml of water. Stock Solution C was prepared by dissolving 150 mg of the herbicide compound in 50 ml of acetone and adding 50 ml of water. Stock Solution D was prepared by adding 10 ml of Stock Solution C to 20 ml of acetone and 20 ml of water. Stock Solution E was prepared by adding 5 ml of Stock Solution C to 22.5 ml of acetone and 22.5 ml of water. Stock Solutions A through E were each added to the respective herbicide stock solutions in a one-to-one v/v ratio. When applied to the flats, Stock Solutions A, B, C, D and E yielded applications rates of 2.52 lb/A, 1.26 lb/A, 0.63 lb/A, 0.126 lb/A and 0.063 lb/A, respectively (2.82, 1.41, 0.70, 0.141, and 0.070 kg/ha).

Nineteen days after seeding, the flats were sprayed with each of the herbicide solutions admixed with each of the stock solutions. Plants were rated 23 days after treatment. The results of this treatment are described in Table III.

TABLE III

Herbicide: 2-chloro-N—[(4-methyloxy-6-methyl-1,3,5-triazin-2-yl)-aminocarbonyl]-benzene sulfonamide
Antidote: 2,2,5-trimethyl-3-dichloroacetyl oxazolidine

| Antidote Application Rate (lb/A) | Corn | % Injury U (%) | % Injury T (%) | % Improvement U-T (%) | % Improvement U-T/U (%) |
|---|---|---|---|---|---|
| Herbicide Application Rate at 0.079 lb/A: | | | | | |
| 2.52 | XL43A | 80 | 25 | 55 | 69 |
| 2.52 | XL55N | 70 | 25 | 45 | 64 |
| 2.52 | XL379 | 70 | 30 | 40 | 57 |
| 1.26 | XL43A | 80 | 25 | 55 | 69 |
| 1.26 | XL55N | 70 | 25 | 45 | 64 |
| 1.26 | XL379 | 70 | 30 | 40 | 57 |
| 0.63 | XL43A | 80 | 45 | 35 | 44 |
| 0.63 | XL55N | 70 | 45 | 25 | 34 |
| 0.63 | XL379 | 70 | 50 | 20 | 26 |
| 0.126 | XL43A | 80 | — | — | — |
| 0.126 | XL55N | 70 | — | — | — |
| 0.126 | XL379 | 70 | — | — | — |
| 0.063 | XL43A | 80 | — | — | — |
| 0.063 | XL55N | 70 | — | — | — |
| 0.063 | XL379 | 70 | — | — | — |
| Herbicide Application Rate at 0.158 lb/A: | | | | | |
| 2.52 | XL43A | 100 | 35 | 65 | 65 |
| 2.52 | XL55N | 100 | 40 | 60 | 60 |
| 2.52 | XL379 | 100 | 50 | 50 | 50 |
| 1.26 | XL43A | 100 | 40 | 60 | 60 |
| 1.26 | XL55N | 100 | 45 | 55 | 55 |
| 1.26 | XL379 | 100 | 50 | 50 | 50 |
| 0.63 | XL43A | 100 | 75 | 25 | 25 |
| 0.63 | XL55N | 100 | 60 | 40 | 40 |
| 0.63 | XL379 | 100 | 65 | 35 | 35 |
| 0.126 | XL43A | 100 | 90 | 10 | 10 |
| 0.126 | XL55N | 100 | 90 | 10 | 10 |
| 0.126 | XL379 | 100 | 95 | 5 | 5 |
| 0.063 | XL43A | 100 | — | — | — |
| 0.063 | XL55N | 100 | — | — | — |
| 0.063 | XL379 | 100 | — | — | — |

U = Treated with herbicide but not treated with antidote.
T = Treated with herbicide and antidote
— = Dashes indicate injury rate ≧ U.

EXAMPLE IV

Use on Corn at Various Times After Seeding

Flats were prepared for planting as above except that only corn seeds of DeKalb corn strain XL43A were planted. Seeds of 3 representative weeds, annual morningglory (*Ipomoea purpurea*), velvetleaf (*Abutilon theophrasti*) and cockelbur (*Xanthium sp.*) were also planted. Planting times were staggered at weekly intervals to allow plants of differing maturity to be sprayed in a single application and rated at one time. After planting, the flats were maintained as in the examples above. Stock solutions of the herbicide compound were prepared by dissolving a preselected amount of the herbicide compound in water. Stock solutions of the antidote compound were prepared in like manner. Spray solutions having approximately 25 ml of each herbicide stock solution and 25 ml of each antidote stock solution were applied to the soil or foliage surface at 0, 1, 2, and 3 weeks after seeding of the flats. The appropriate stock solution of herbicide compound and antidote were tank mixed and applied at the rates of 2.0, 1.0, 0.5, 0.25 and 0.1 pounds per acre (2.24, 1.12, 0.56, 0.28, and 0.11 kg/ha) of antidote compound and 0.0625 or 0.125 pounds per acre (0.070 or 0.137 kg/ha) of herbicide compound. Plants were rated 35 days after treatment. The results of the treatment are found in Table IV. Greater rates of crop plant survival are observed when the composition is used pre-emergently or soon after planting in corn. No significant survival of the representation weeds was observed.

duced cessation of life. The term "herbicidally effective amount" describes the amount of an herbicide compound which controls or modifies plant growth as defined above. In general, the herbicide is applied at a rate of between about 0.010 and 50 lb/acre (0.011 to 56 kg/ha), but the rate may vary within this range. Preferably, the herbicide is applied at a range between 0.0156 to 0.160 lb/acre (0.0174 to 0.179 kg/ha). The actual amount used depends upon several considerations, including particular weed susceptibility, overall cost limitations, activity towards crops, and the particular herbicide compound used.

The precise mechanism by which an antidote reduces herbicidal crop injury has not been established. An

TABLE IV

Herbicide Composition Effect on Corn and Selected Weeds Applied at Various Times After Seeding Herbicide: 2-chloro-N—[(4-methyloxy-6-methyl-1,3,5-triazin-2-yl)-aminocarbonyl]-benzene sulfonamide
Antidote: 2,2,5-trimethyl-3-dichloroacetyloxazolidine
Method: postseeding

| Herbicide Rate (lb/A) | Antidote Rate (lb/A) | Weeks | Corn XL43A | | | Annual Morning glory | | | Velvet leaf | | | Cocklebur | | |
|---|---|---|---|---|---|---|---|---|---|---|---|---|---|---|
| | | | U | T | % | U | T | % | U | T | % | U | T | % |
| 0.0625 | 0.1 | 0 | 100 | 93 | 7 | 99 | 99 | — | 100 | 100 | — | 100 | 100 | — |
| 0.0625 | 0.25 | 0 | 100 | 89 | 11 | 99 | 99 | — | 100 | 99 | 1 | 100 | 100 | — |
| 0.0625 | 0.5 | 0 | 100 | 83 | 17 | 99 | 100 | — | 100 | 99 | 1 | 100 | 100 | — |
| 0.0625 | 1.0 | 0 | 100 | 62 | 38 | 99 | 100 | — | 100 | 100 | — | 100 | 100 | — |
| 0.0625 | 2.0 | 0 | 100 | 62 | 38 | 99 | 100 | — | 100 | 100 | — | 100 | 100 | — |
| 0.0625 | 0.1 | 0 | 100 | 95 | 5 | 100 | 100 | — | 100 | 100 | — | 100 | 100 | — |
| 0.0625 | 0.25 | 0 | 100 | 75 | 16 | 100 | 100 | — | 100 | 100 | — | 100 | 100 | — |
| 0.0625 | 0.5 | 0 | 100 | 63 | 37 | 100 | 100 | — | 100 | 100 | — | 100 | 100 | — |
| 0.0625 | 1.0 | 0 | 100 | 62 | 38 | 100 | 100 | — | 100 | 100 | — | 100 | 100 | — |
| 0.0625 | 2.0 | 0 | 100 | 55 | 45 | 100 | 100 | — | 100 | 100 | — | 100 | 100 | — |
| 0.0625 | 0.1 | 1 | 100 | 95 | 5 | 95 | 100 | — | 100 | 100 | — | 100 | 100 | — |
| 0.0625 | 0.25 | 1 | 100 | 92 | 8 | 95 | 95 | — | 100 | 100 | — | 100 | 100 | — |
| 0.0625 | 0.5 | 1 | 100 | 89 | 11 | 95 | 100 | — | 100 | 100 | — | 100 | 100 | — |
| 0.0625 | 1.0 | 1 | 100 | 83 | 17 | 95 | 90 | 5 | 100 | 100 | — | 100 | 100 | — |
| 0.0625 | 2.0 | 1 | 100 | 80 | 20 | 95 | 100 | — | 100 | 100 | — | 100 | 100 | — |
| 0.125 | 0.1 | 1 | 100 | 100 | — | 100 | 100 | — | 100 | 100 | — | 100 | 100 | — |
| 0.125 | 0.25 | 1 | 100 | 99 | 1 | 100 | 100 | — | 100 | 100 | — | 100 | 100 | — |
| 0.125 | 0.5 | 1 | 100 | 83 | 17 | 100 | 100 | — | 100 | 100 | — | 100 | 100 | — |
| 0.125 | 1.0 | 1 | 100 | 80 | 20 | 100 | 100 | — | 100 | 100 | — | 100 | 100 | — |
| 0.125 | 2.0 | 1 | 100 | 97 | 3 | 100 | 100 | — | 100 | 100 | — | 100 | 100 | — |
| 0.0625 | 0.1 | 2 | 100 | 96 | 4 | 100 | 100 | — | 100 | 100 | — | 100 | 100 | — |
| 0.0625 | 0.25 | 2 | 100 | 88 | 12 | 100 | 100 | — | 100 | 100 | — | 100 | 100 | — |
| 0.0625 | 0.5 | 2 | 100 | 78 | 22 | 100 | 100 | — | 100 | 100 | — | 100 | 100 | — |
| 0.0625 | 1.0 | 2 | 100 | 70 | 30 | 100 | 100 | — | 100 | 100 | — | 100 | 100 | — |
| 0.0625 | 2.0 | 2 | 100 | 70 | 30 | 100 | 100 | — | 100 | 100 | — | 100 | 100 | — |
| 0.125 | 0.1 | 2 | 100 | 87 | 13 | 95 | 100 | — | 100 | 100 | — | 100 | 100 | — |
| 0.125 | 0.25 | 2 | 100 | 87 | 13 | 95 | 95 | — | 100 | 100 | — | 100 | 100 | — |
| 0.125 | 0.5 | 2 | 100 | 91 | 9 | 95 | 95 | — | 100 | 100 | — | 100 | 100 | — |
| 0.125 | 1.0 | 2 | 100 | 87 | 13 | 95 | 100 | — | 100 | 100 | — | 100 | 100 | — |
| 0.125 | 2.0 | 2 | 100 | 83 | 17 | 95 | 100 | — | 100 | 100 | — | 100 | 100 | — |
| 0.125 | 0.1 | 3 | 100 | 100 | — | 98 | 100 | — | 100 | 100 | — | 100 | 100 | — |
| 0.125 | 0.25 | 3 | 100 | 95 | 5 | 98 | 100 | — | 100 | 100 | — | 100 | 100 | — |
| 0.125 | 0.5 | 3 | 100 | 90 | 10 | 98 | 98 | — | 100 | 100 | — | 100 | 100 | — |
| 0.125 | 1.0 | 3 | 100 | 90 | 10 | 98 | 100 | — | 100 | 100 | — | 100 | 100 | — |
| 0.125 | 2.0 | 3 | 100 | 100 | — | 98 | 100 | — | 100 | 100 | — | 100 | 100 | — |
| 0.0625 | 0.25 | 3 | 100 | 89 | 11 | 95 | 95 | — | 100 | 100 | — | 100 | 100 | — |
| 0.0625 | 0.5 | 3 | 100 | 90 | 10 | 95 | 95 | — | 100 | 100 | — | 100 | 100 | — |
| 0.0625 | 1.0 | 3 | 100 | 93 | 7 | 95 | 100 | — | 100 | 100 | — | 100 | 100 | — |
| 0.0625 | 2.0 | 3 | 100 | 97 | 3 | 95 | 95 | — | 100 | 100 | — | 100 | 100 | — |

U = % Injury to weed or crop plants treated with herbicide but not treated with antidote.
T = % injury to weed or crop plants treated with herbicide and antidote
% = Percent Improvement (U–T)
— = Dashes indicate injury rate ≧ U.

As used herein, the term "herbicide" means a compound which controls or modifies plant growth, e.g., killing, retarding, defoliating, dessicating, regulating, stunting, tillering, stimulating, and dwarfing. The term "plant" refers to all physical parts of a plant, including seeds, seedlings, saplings, roots, tubers, stems, stalks, foliage and fruits. "Plant Growth" includes all phases of development from seed germination to natural or inantidote compound may be a remedy, interferant, protectant, or antagonist. As used herein, "antidote" describes a compound which has the effect of establishing herbicide selectivity, i.e., continued herbicidal phytotoxicity to weed species and reduced or non-phytotoxicity to cultivated crop species. The term "antidotally effective amount" describes the amount of an antidote compound which counteracts a phytotoxic response to a beneficial crop to an herbicide. In general, the antidote is applied at a rate of between about 0.1 to 50 lb/acre (0.112 to 56 kg/ha). The actual amount of antidote used depending upon several concentrations including, in particular, crop selectivity, weed susceptability, overall cost limitations, and the particular antidote compound used.

The herbicidal compounds employed in the method of this invention are active herbicides of a general type. That is, the members are classes are herbicidally effective against a wide range of plant species with no discrimination between desirable and undesirable species. The method of controlling vegetation comprises applying an herbicidally effective amount of the herein described herbicidal compounds to the area or plant locus where control is desired, and an antidotally effective amount of the herein described antidote compound. Alternatively, the antidote compound described herein may be applied to the plant seed prior to planting, the antidote compound being antidotally effective with the herbicide compound.

It is clear that the class of herbicide compounds described and illustrated herein is characterized by effective herbicides exhibiting such activity. The degree of this herbicidal activity varies amongst specific compounds. Similarly, the degree of activity to some extent varies among the species of plants to which a specific herbicidal compound or combination may be applied. Thus selection of a specific herbicidal compound or combination to control undesirable plant species readily may be made. Within the present invention, the reduction of injury to a desired crop species in the presence of this class of compounds may be achieved. The beneficial plant species which can be protected by this method is not intended to be limited by the specific crops employed in the examples.

Formulations

A formulation is the incorporation of a formulant in a form which is directly usable on crops and weeds. As defined herein, a "formulant" is the material which is to be formulated. The formulant may be either an antidote compound alone, the antidote compound being antidotally effective with the herbicide compound, or an herbicide and antidote composition. The purpose of the formulation is to apply the formulant to the locus where it is desired to establish herbicidal selectivity by a convenient method. The "locus" may include soil, seeds, seedlings and vegetation. The formulations are commonly dusts, wettable powders, granules, solutions or emulsifiable concentrates.

Dusts are free-flowing powder compositions containing the formulant impregnated on a particulate carrier. The particle size of the carrier is usually in the approximate range of 30 to 50 microns. Examples of suitable carriers are talc, bentonite, diatomaceous earth and pyrophyllite. The composition generally contains up to 50% of formulant. Anti-caking and anti-static agents may also be added. Dust may be applied by spraying from boom and hand sprayers on airplanes.

Wettable powders are finely divided compositions comprising a particulate carrier impregnated with the formulant and additionally containing one or more surface active agents. The surface active agent permits a more rapid dispersion of the powder in an aqueous medium to form stable, sprayable suspensions. A wide variety of surface active agents can be used, for example, long chain fatty alcohols and alkali metal salts of the sulfated fatty alcohols; salts of sulfonic acids; esters of long chain fatty acids; and polyhedric alcohols, in which the alcohol groups are free-omega substituted polyethyleneglycols of relatively long chain length. A list of surface active agents suitable for use in agricultural formulations can be found in Wade Van Valkenburg, Pesticide Formulations (Marcel Dekker, Inc., New York, 1973), pages 79–84.

Granules comprise the formulant impregnated on a particulate inert carrier having a particle size of about 1 to 2 millimeters in diameter. The granules can be made by spraying a solution of the formulant in a volatile solvent onto the granular carrier. Examples of suitable carriers for the preparation of granules include clay, vermiculate, sawdust and granular carbon.

Emulsifiable concentrates consist of an oil solution of the formula plus an emulsifying agent. Prior to use, the concentrate is diluted with water to form a suspended emulsion of oil droplets. The emulsifier is used in a mixture of anionic or nonionic surfactants. Other additives, such as suspending agents and thickeners, may be included in the emulsifiable concentrate.

Formulations generally contain several additives in addition to the formulant and carrier or agent. Among these are inert ingredients, diluent carriers, organic solvents, water, oil and water, water in oil emulsions, carriers of dusts and granules and surface active wetting, dispersing and emulsifying agents. Fertilizers, e.g., ammonium nitrate, urea and superphosphate, may be included. Aids to rooting and growth, e.g., compost, manure, humus and sand may also be included. Alternatively, the antidote compounds and herbicide and antidote compositions of this invention can be applied to a crop by addition of the formulant to irrigation water supplied to the field to be treated. As another alternative, the formulant can be applied to the soil in the form of the solution in a suitable solvent. Solvents frequently used in formulations include kerosene, fuel oil, xylene, petroleum fractions with boiling ranges above xylene and aromatic petroleum fractions rich in methylated naphthalenes. Thick solutions and light dusts, may be applied by spraying from boom and hand sprayers or airplanes.

What is claimed is:

1. An herbicidal composition comprising an herbicidally effective amount of an herbicide compound having the formula

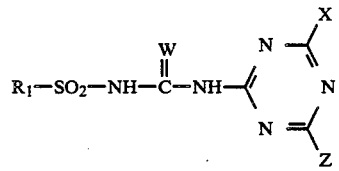

wherein
$R_1$ is

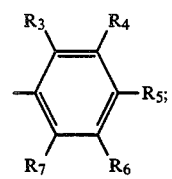

R3 and R6 are independently hydrogen, halogen, alkyl, alkoxy, nitro, trifluoroalkyl, cyano, $CH_3S(O)_n-$ or $CH_3CH_2S(O)_n-$;

R4 is hydrogen, halogen, or alkyl;

R5 is hydrogen, halogen, alkoxy or alkoxy;

R7 is hydrogen, halogen, alkyl, or alkoxy

N is 0, 1 or 2;

W is sulfur or oxygen;

X is hydrogen, halogen, alkyl, trifluoroalkyl, thioalkyl, or alkoxyalkyl; and

Z is alkyl or alkoxy; or their ariculturally acceptable salts; and an antidotally effective amount of an antidote compound having the formula

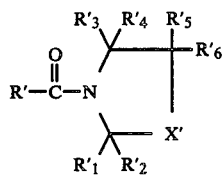

in which

X' is oxygen or sulfur, R' is haloalkyl having 1 to 10 carbon atoms, inclusive, and the term halo includes chloro and bromo substitutions, alkyl having 1 to 10 carbon atoms, inclusive, or alkylthio having 1 to 4 carbon atoms, inclusive, $R'_1$, $R'_2$, $R'_3$, $R'_5$ and $R'_6$ are independently selected from the group consisting of hydrogen, lower alkyl having 1 to 4 carbon atoms, inclusive, alkoxyalkyl having a total of 2 to 4 carbon atoms, inclusive, and lower alkylol having 1 to 4 carbon atoms, inclusive.

2. The composition of claim 1 wherein R7 is chlorine; W is oxygen; X is methyloxy; and Z is methyl.

3. The composition of claim 2 wherein R' is dichloromethyl.

4. The method of controlling weeds pests and protecting crop plants comprising adding to the habitat thereof an herbicidally effective amount of the composition of claim 1.

5. The method of claim 4 wherein R7 is chlorine; W is oxygen; X is methyloxy; and Z is methyl.

6. The method of claim 5 wherein R' is dichloromethyl.

7. The method of claim 4 wherein said composition is applied pre-emergently to the soil containing seeds of said crop plants.

8. The method of claim 7 wherein said seeds are corn seeds.

9. The method of claim 4 wherein said composition is applied post-emergently to the soil containing said crop plants.

10. The method of claim 9 wherein said crop plants are corn.

11. The method of claim 4 wherein said composition is applied to the foliage of said crop plants.

12. The method of claim 11 wherein said crop plants are corn.

13. The method of protecting a crop plant from injury due to an herbicidally active herbicide compound having the formula:

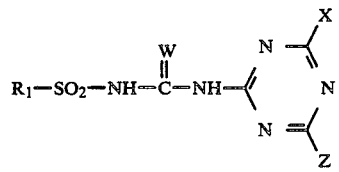

wherein
R1 is

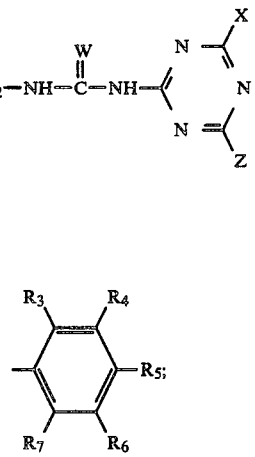

R3 and R6 are independently hydrogen, halogen, alkyl, alkoxy, bromine, iodine, alkyl of 1-4 carbon atoms, alkoxy of 1-4 nitro, trifluoroalkyl, cyano, $CH_3S(O)_n-$ or $CH_3CH_2S(O)_n-$;

R4 is hydrogen, halogen, or alkyl

R5 is hydrogen, halogen, alkyl or alkoxy;

R7 is hydrogen, halogen, alkyl, or alkoxy;

W is oxygen or sulfur;

n is 0, 1 or 2;

X is hydrogen, halogen, alkyl, alkoxy, trifluoroalkyl, thioalkyl, or alkoxyalkyl; and Z is alkyl or alkoxy; or their agriculturally acceptable salts; comprising applying to the plant seed prior to planting a non-phytotoxic amount of an antidote compound having the formula

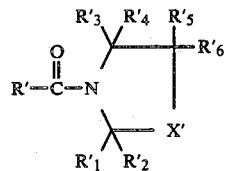

in which

X' is oxygen or sulfur, R' is haloalkyl having 1 to 10 carbon atoms, inclusive, and the term halo includes chloro and bromo substitutions, alkyl having 1 to 10 carbon atoms, inclusive, or alkylthio having 1 to 4 carbon atoms, inclusive, $R'_1$, $R'_2$, $R'_3$, $R'_5$ and $R'_6$ are independently selected from the group consisting of hydrogen, lower alkyl having 1 to 4 carbon atoms, inclusive, alkoxyalkyl having a total of 2 to 4 carbon atoms, inclusive, and lower alkylol having 1 to 4 carbon atoms, inclusive, said antidote compound being antidotally effective with said herbicide compound.

14. The method of claim 7 wherein R7 is chlorine; W is oxygen; X is methyloxy; and Z is methyl.

15. The method of claim 8 wherein R' is dichloromethyl.